United States Patent [19]

Burke

[11] Patent Number: 4,788,333

[45] Date of Patent: * Nov. 29, 1988

[54] HYDROCARBOXYLATION OF UNSATURATED CARBOXYLIC ACIDS TO LINEAR DICARBOXYLIC ACIDS

[75] Inventor: Patrick M. Burke, Wilmington, Del.

[73] Assignee: E. I. Du Pont de Nemours and Company, Wilmington, Del.

[*] Notice: The portion of the term of this patent subsequent to Nov. 11, 2003 has been disclaimed.

[21] Appl. No.: 689,165

[22] Filed: Jan. 7, 1985

[51] Int. Cl.$^4$ .............................................. C07C 51/14
[52] U.S. Cl. .................................... 562/517; 562/522
[58] Field of Search ................................ 562/517, 522

[56] References Cited

U.S. PATENT DOCUMENTS

| | | | |
|---|---|---|---|
| 3,579,552 | 5/1971 | Craddock et al. | 260/413 |
| 3,876,695 | 4/1975 | Kutepow | 562/522 |
| 4,172,087 | 10/1979 | Knifton | 260/410.6 |
| 4,377,708 | 3/1983 | Morris | 560/266 |
| 4,622,423 | 11/1986 | Burke | 562/522 |

FOREIGN PATENT DOCUMENTS

| | | |
|---|---|---|
| 0075524 | 3/1983 | European Pat. Off. . |
| 3040432 | 6/1981 | Fed. Rep. of Germany . |
| 92913 | 7/1979 | Japan . |
| 1092694 | 2/1965 | United Kingdom . |
| 2014136A | 8/1979 | United Kingdom . |

OTHER PUBLICATIONS

Imyanitov et al., Karbonili–rovonie Nenasyshchennyky Uglevodorodov (1968), 225–32, CA 71 21648y.
Mechanistic Pathways in the Catalysis of Olefin Hydrocarboxylation by Rhodium, Iridium, and Cobalt Complexes, D. Forster et al., Catal. Rev.–Sci. Eng., 23 (1&2), pp. 89–105 (1981).

Primary Examiner—Werren B. Lone

[57] ABSTRACT

The preparation of linear dicarboxylic acids, e.g., adipic acid, by hydrocarboxylating unsaturated monocarboxylic acids, e.g., 3-pentenoic acid, with carbon monoxide and water in the presence of a rhodium-containing catalyst, an iodide promoter and certain inert halocarbon solvents, e.g., methylene chloride.

8 Claims, No Drawings

HYDROCARBOXYLATION OF UNSATURATED CARBOXYLIC ACIDS TO LINEAR DICARBOXYLIC ACIDS

BACKGROUND OF THE INVENTION

1. Field of the Invention

The present invention relates to the preparation of linear dicarboxylic acids, e.g., adipic acid, by hydrocarboxylating unsaturated monocarboxylic acids. e.g., 3-pentenoic acid, with carbon monoxide and water in the presence of a rhodium-containing catalyst, an iodide promoter and certain inert halocarbon solvents, e.g., methylene chloride.

2. Description of the Prior Art

U.S. Pat. No. 3,876,695, issued on Apr. 8, 1975 to Nicholaus Von Kutepow, discloses a process for the production of adipic acid by the reaction of butadiene, carbon monoxide and water using certain rhodium carbonyl complexes along with free or combined halogen as a catalyst system. The patentee discloses the advantage of using a solvent in the system which is a nonsolvent for adipic acid and cites as operable aromatic hydrocarbons, e.g., xylene, saturated cycloaliphatic hydrocarbons, e.g., cyclohexane and saturated aliphatic hydrocarbons, preferably those having 8-12 carbon atoms. The patentee suggests introducing catalyst in aqueous solution when practicing the process continuously. In Column 1, lines 10-50, the patentee discusses representative art on the preparation of acids and esters via carbonylation.

U.S. Pat. No. 4,172,087, issued on Oct. 23, 1979 to J. F. Knifton discloses a process for the carbonylation and concurrent dimerization of olefins such as 1,3-butadiene in the presence of hydroxylated coreactants, a dual function palladium catalyst and a tertiary nitrogen-containing base to produce acids and ester derivatives of unsaturated carboxylic acids. The reaction of butadiene is taught to produce 3-pentenoic acid and 3,8-nonadienoic acid and their corresponding ester derivatives. The patentees do not discuss the desirability and/or effect of conducting the reaction in the presence of a solvent. The catalyst system requires the presence of ligands of Group VB elements to stabilize the palladium salts. Included in these ligands are numerous phosphorus-containing compounds, e.g., bis(1,2-diphenylphosphino)ethane.

European Pat. No. 0075524, published on Mar. 30, 1983 and assigned to Rhone-Poulenc Chimie De Base, discloses a process for the preparation of beta, gamma unsaturated carboxylic acids by the carbonylation of conjugated dienes using a palladium catalyst with a halide promoter to produce the corresponding esters.

Japanese Pat. 92,913 (unexamined) published on July 23, 1979 discloses the carbonylation of lactones to carboxylic acids using a platinum group metal, e.g., rhodium, promoted with iodine compounds. The patentees do not recognize any criticality with respect to the amount of water present and employ acetic acid as a solvent.

The production of 3-pentenoic acid is discussed in an article by Imyanitov et al., Karbonili-rovonie Nenasyshchennykh Uglevodorodov (1968) 225-32, CA 71 216484, a portion of which disclosure appears in U.K. Pat. 1,092,694 published on Feb. 4, 1965. The reaction was studied in a pyridine solvent with cobalt carbonyl catalysts under a pressure of 120-500 atmospheres. The authors note that the order with respect to water changes from approximately zero where the reaction mixture comprises equal molar amounts of water to −1 order at a 13-fold excess of water. The preparation of the esters of 3-pentenoic acid using cobalt catalysts is disclosed in German Patent DE 3040432, published on June 19, 1981. Hydrocarboxylations employing rhodium catalysts are discussed in the article *Mechanistic Pathways in the Catalysis of Olefin Hydrocarboxylation by Rhodium, Iridium, and Cobalt Complexes*, D. Forster et al., Catal. Rev.—Sci, Eng. 23(1&2) pp. 89–105 (1981).

U.S. Pat. No. 3,579,552 discloses the use of rhodium catalyst with an iodide promoter to prepare carboxylic acids from olefins and other ethylenically unsaturated compounds. In Column 8, lines 31-42, the patentees disclose that an excess of water is beneficial to the reaction which, according to the teachings of the patent, is conducted using the olefins themselves or carboxylic acids as solvent. Example 9 demonstrates the employment of acetic acid as a solvent for the reaction of butadiene. In all cases a significant percentage of the products are branched.

SUMMARY OF THE INVENTION

The present invention is a process for the preparation of linear dicarboxylic acids, e.g., adipic acid by the reaction of unsaturated monocarboxylic acids, e.g., 3-pentenoic acid, carbon monoxide and water in the presence of a rhodium-containing catalyst, an iodide promoter and certain of the halocarbon solvents which have 1-2 carbon atoms, e.g., methylene chloride, at a temperature in the range 100°–240° C. and a pressure in the range 14–240 atm.

The unsaturated monocarboxylic acid has the general formula

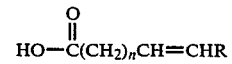

wherein R is selected from the class consisting of hydrogen, methyl and ethyl and n is 0-8 and preferably 0-2.

The amount of water in the reaction medium is maintained at less than about 4.3% and preferably less than 3.5% by weight based upon the weight of the solvent in order to maintain catalyst activity and to assure a high yield.

In one preferred embodiment 0.2-2.0% by weight based upon the weight of the reaction medium of an acid scavenger, preferably an alcohol, diol or triol, e.g., methanol, ethylene glycol and glycerol is present in the reaction medium.

DETAILED DESCRIPTION OF THE INVENTION

In the hydrocarboxylation of olefins emphasis has been placed upon the production of adipic acid directly from butadiene because this compound is an intermediate for nylon polymers.

It has been found that the yield to the desired linear dicarboxylic acids, e.g., adipic acid, can be improved if the reaction is conducted in two steps. In the first step unsaturated monocarboxylic acids, e.g., 3-pentenoic acid are produced which are then hydrocarboxylated in a second step to linear dicarboxylic acids, e.g., adipic acid in exceptionally high yields and under relatively mild conditions. This application is directed to the second step. In addition, it should be noted that the selectivity to the linear acids is quite high in the process of the present invention, in most cases exceeding 50% with the principal carbonylated byproduct being α-methylglutaric acid.

The unsaturated monocarboxylic acids which are operable in the present invention have the general formula

wherein R is selected from the class consisting of hydrogen, methyl and ethyl and n is 0-8 and preferably 0-2. Such acids include 2-, 3- and 4-pentenoic acid, 3-butenoic acid, acrylic acid, 3-hexenoic acid, and undecylenic acid. Other useful acids include 2-methyl-2-butenoic acid and 2-methyl-3-butenoic acid.

The source of the reactants for the present process is not particularly critical. Commercially available grades of carbon monoxide and unsaturated monocarboxylic acids are quite satisfactory.

The reaction can be conducted over a reasonably wide temperature range, but relatively mild conditions are preferred. Acceptable yield is realized at temperatures in the range 100°-240° C. and preferably 150°-180° C. Temperatures above the upper end of the range result in a significant reduction in the conversion to diacid. At temperatures below the lower end of the range, the reaction is too slow to be economic.

Relatively moderate pressures, i.e., in the range 14-240, preferably 24-40 atm are satisfactory. The partial pressure of carbon monoxide is usually maintained in the range 10-35 atm and preferably 10-17 atm.

The catalyst precursor employed can be any rhodium complex that is free of interfering ligands particularly bidentate phosphine and nitrogen ligands. Rhodium complexes such as rhodium(III) chloride-$RhCl_3 \cdot 3H_2O$, rhodium (III) iodide-$RhI_3$, rhodium carbonyliodide-$Rh(CO)_nI_3$ (n=2-3), rhodium(III) nitrate-$Rh(NO_3)_3 \cdot 2H_2O$, dodecacarbonyltetrarhodium(O)-$Rh_4(CO)_{12}$, acetylacetonatodicarbonylrhodium(I)-$Rh(CO)_2(C_5H_7O_2)$, chlorobis(ethylene)rhodium(I) dimer-$[Rh(C_2H_4)Cl]_2$, acetylacetonato(1,5-cyclooctadiene)rhodium(I)$Rh(C_8H_{12})(C_5H_7O)_2$, chlorocarbonylbis(triphenylphosphine) rhodium(I)$RhCl(CO)(PPh_3)_2$, hexadecacarbonylhexarhodium(O)-$Rh_6(CO)_{16}$, tris(acetylacetonato)rhodium(III)-$Rh(C_5H_7O_2)_3$, rhodium(II)octanoate dimer-$Rh_2[CO_2(CH_2)_6 CH_3]_4$, chlorodicarbonylrhodium(I) dimer- $[Rh(CO)_2Cl]_2$, chloro(1,5-cyclooctadiene)- rhodium(I)dimer-$[Rh(C_8H_{12})Cl]_2$, acetylacetonatobis(ethylene)rhodium(I)$Rh(C_2H_4)_2(C_5H_7O_2)$ and rhodium(II)acetate dimer$Rh_2(CO_2CH_3)_4$ are operable.

The concentration of catalyst precursor is not critical but is usually maintained in the range 0.04-0.16% by weight of rhodium metal based upon the weight of the reaction medium. The weight of the reaction medium includes the weight of solvent internal standard, catalyst, promoter and reactants. The catalyst which can be preformed or can be formed in situ, must be promoted, preferably by iodide, to achieve a satisfactory reaction rate. Alkyl iodides having 1-7 carbon atoms are preferred promoters at the higher reaction temperatures. Methyl iodide is especially preferred. Other suitable promoters include hydrogen iodide, iodoethane, 1-iodobutane, 1,4-di-iodobutane, 2-iodopropane, 1-iodopropane and iodoheptane. As believed apparent from the foregoing, the promoter and rhodium can be present in the same compound as in rhodium iodide. Generally the concentration of promoter is between 0.1-1.0% by weight iodide based upon the weight of the reaction medium and at a mole ratio to rhodium in the range 3/1 to 50/1, preferably 5/1 to 15/1.

The reaction is carried out in the presence of a solvent the selection of which is critical to the present invention. Coordinating solvents, e.g., pyridine, dimethylformamide, dimethylsulfoxide and N-methylpyrrolidone block the active sites on the rhodium and should be avoided. Solvents such as acetic acid are also undesirable because linear selectivity is low in their presence. Nonpolar solvents such as cyclohexane and toluene are undesirable because they promote the formation of branched products and the shift reaction, the latter resulting in the formation of undesired monocarboxylic acids. It is important that the solvent be essentially inert to the reactants and resist hydrolysis. The preferred solvents include saturated halocarbon, except fluorocarbon and preferably chlorocarbon, solvents and mixtures thereof having 1-2 carbon atoms, e.g., methylene chloride, 1,1,2,2-tetrachloroethane, 1,1,2-trichloroethane, 1,1-dichloroethane, chloroform and carbon tetrachloride. In order to emphasize hydrolysis resistance, the operable solvents within the purview of the foregoing description are further characterized in that when the solvent has two carbon atoms not more than two halogen atoms are attached to each carbon atom. Methylene chloride is the preferred solvent. The amount of solvent employed can vary widely, e.g., 50-99, usually 80-99 and preferably 85-95% by weight based upon the weight of the reaction mixture.

In one especially preferred embodiment from 0.2-2.0, preferably 0.5-1.0% by weight based upon the weight of the solvent of an acid scavenger is introduced into the reaction medium. Preferred scavengers include alcohols such as alkyl alcohols having 1-6 carbon atoms wherein the hydroxyl function is primary or secondary, e.g., methyl alcohol, ethyl alcohol, isopropyl alcohol, n-butyl alcohol, isobutyl alcohol and secondary butyl alcohol; diols having 2-4 carbon atoms, e.g., ethylene glycol, propylene glycol and butanediol; triols having 3-4 carbon atoms, e.g., glycerol and 1,2,4-trihydroxybutane. Methyl alcohol is preferred. The alcohol retards catalyst degradation and permits operation at relatively higher temperatures to increase the yield of linear products without as much reduction in conversion as is normally associated with increasing temperatures.

The amount of water in the reaction medium is critical to the present invention and must not exceed 4.3% by weight based upon the weight of the solvent. Preferably the water level is maintained at less than 3.5% on the same basis. The reaction can be carried out batchwise or continuously.

The following examples are presented to illustrate but not to restrict the present invention. Parts and percentages are by weight and the products were analyzed by gas chromatography as the methyl esters unless otherwise noted.

EXAMPLE 1

A 300 ml mechanically stirred reactor constructed of Hastelloy-C was flushed with nitrogen followed by high purity carbon monoxide and then charged with 150 ml of methylene chloride containing 15 g of 3-pentenoic acid, 2.13 g methyl iodide, 5.0 g o-dichlorobenzene (as an internal standard) and 1.8 g of isopropanol. The reactor was closed and the pressure therein was increased to 13.6 atm with carbon monoxide. The reactor was then heated until the temperature of the contents reached 173° C. whereupon a solution of 0.40 g of rhodium chloride in 6.0 ml of water was injected into the reactor. After this injection was complete, the pressure of the reactor was increased to 27.2 atm with carbon monoxide and maintained at that pressure and at a temperature of 173° C. during the hydrocarboxylation. The consumption of carbon monoxide was monitored and the reaction was terminated after two hours when the consumption of carbon monoxide ceased, (approximately 95% of the theoretical amount). The contents of the reactor were recovered by cooling the reactor to approximately 20° C. and slowly venting the reactor to the atmosphere. The reactor contents were removed and the reactor was washed with 350 ml of methanol under pressure at a temperature of 100° C. The wash liquid and reactor contents were combined, diluted to 500 ml volume with methanol. Analysis indicated that 97.0% conversion of the 3-pentenoic acid was obtained. The product contained 66.2% adipic acid, 17.3% α-methylglutaric acid, 3.4% ethylsuccinic acid, 5.1% 2-pentenoic acid and 9.4% γ-valerolactone.

In order to demonstrate the adverse effect of excessive water, the procedure in Example 1 was repeated, except that the isopropanol was replaced by 15 mmoles (0.95 g) of methanol and the amount of water was increased to 9.0 ml, i.e., 9 g water and 150 ml $CH_2Cl_2$ solvent, or about 4.3% by weight based upon the weight of the solvent. Uptake of CO was 10% of theoretical after 2 hours. No additional uptake occurred after a further 3 hours, indicating that the catalyst had become completely deactivated.

Product analysis showed 6.8% conversion to diacids, of which 5.4% was adipic acid (78.7% linearity).

EXAMPLES 2-9

To a 200 ml shaker-tube reactor constructed of Hastelloy-C was charged 100 ml methylene chloride, solution containing 10.0 g 4-pentenoic acid, 2.48 g methyl iodide, 2.0 g benzoic acid (internal standard) along with 2 ml of an aqueous solution containing 0.264 g of rhodium chloride. The shaker tube was pressurized to 6.8 atm with carbon monoxide and the contents were heated to the temperature indicated in Table I. The pressure was increased with carbon monoxide to that indicated in Table I and maintained at that pressure for a period of one hour after no further pressure drop was observed. The contents of the shaker tube were cooled to room temperature and the tube slowly vented to the atmosphere following which the contents were analyzed by gas chromotography as the trimethylsilyl derivatives. The results are reported in Table I.

Repetition of Example 2 using 1,4-diiodobutane, iodomethane, iodoethane, iodobutane, 2-iodopropane, 1-iodopropane and 1-iodoheptane as a promoter gave results essentially the same as the methyl iodide promoter.

EXAMPLES 10-20

Example 2 was repeated using 3-pentenoic acid instead of 4-pentenoic acid under the conditions and with the results reported in Table I.

EXAMPLE 21

The procedure in Example 1 was repeated except that the $RhCl_3$ catalyst was replaced by an equivalent amount, on a g-atom of rhodium basis, of chloro(1,5-cyclooctadiene) rhodium (I) dimer (0.37 g; 1.5 mg—atom of rhodium as $[Rh(COD)Cl]_2$) added to the methylene chloride solution. The isopropanol was replaced by 0.96 g of methanol.

Analysis indicated 92% 3PA conversion, 68% adipic acid yield and 78% linearity.

EXAMPLE 22

The procedure in Example 21 was repeated except that 0.27 g of hexarhodium hexadecacarbonyl $Rh_6(CO)_{16}$ was employed as the catalyst precursor.

Analysis indicated 95.5% conversion, 66.5% adipic acid yield and 77% linearity.

EXAMPLE 23

The procedure in Example 1 was repeated except that the $RhCl_3$ catalyst precursor was replaced by an equivalent amount, on a g-atom rhodium basis, of a methylene chloride-insoluble rhodium carbonyl iodide complex containing 11.8% rhodium and 51.5% iodine and the amount of methyl iodide promoter was increased to 4.26 g (30 mmoles). The reaction temperature was maintained at 165°.

Uptake of CO ceased in about 4 hours.

Analysis indicated 95.4% conversion, 56.4% yield to adipic acid and 68.3% linearity.

EXAMPLE 24

The procedure in Example 1 was repeated except that the isopropanol was omitted. After 3 hours, uptake of C. had essentially ceased.

Analysis indicated that 63% of the 3-pentenoic acid had been converted to diacids, of which 43.6% was adipic acid (78.7% linearity).

EXAMPLE 25

The procedure of Example 1 was repeated except that the isopropanol was replaced by 0.96 g of methanol. The uptake of carbon monoxide was rapid and essentially complete in about two hours.

Analysis indicated 99.4% conversion. 70% yield to adipic acid and a linearity of 82%.

EXAMPLE 26

The procedure of Example 1 was repeated except that the isopropanol was replaced by 0.96 g methanol and the amount of 3-pentenoic acid was increased to 45 g. At the beginning of the reaction 4.6 g of water was added along with the rhodium chloride catalyst and 4.6 g of water was introduced into the reactor over a period of 30 minutes after the uptake of carbon monoxide was about 50% of theoretical.

Analysis indicated a conversion of 97%, a yield to adipic acid of 67.2% and 78% linearity.

EXAMPLE 27

The procedure of Example 2 was repeated except that the olefin was 3-pentenoic acid, the solvent was 1,1,2-trichloroethane and the reaction temperature was 170° C.

The conversion was essentially 100% and the yield to adipic acid was 44.2% with 53% linearity.

EXAMPLE 28

The procedure of Example 27 was repeated except that the solvent was 1,1,2,2-tetrachloroethane.

The conversion was essentially 99% and the yield to adipic acid was 40.1% (46% linearity).

EXAMPLE 29

Example 1 was modified as follows. The reactor was charged with 150 ml of methylene chloride containing 12.9 g 3-butenoic acid, 0.37 g chlorocarbonylrhodium (I) dimer and 10.0 g o-dichlorobenzene (internal standard). The contents of the reactor were heated to 140° C. and a pressure of 22.4 atm was established before the reaction was initiated by injecting 4.1 g of an aqueous solution containing 2.4 g of hydrogen iodide. The temperature and pressure were maintained as indicated during the reaction. The consumption of carbon monoxide ceased in about 20 minutes. After about 90 minutes the reaction mixture was cooled and worked up as in Example 1.

Analysis indicated 45.5% glutaric acid and 22.4% methylsuccinic acid based on the butenoic acid charged. The linearity was 67%.

EXAMPLE 30

Example 1 was repeated, except that the 3-pentenoic acid was replaced with 17.1 g of trans-3-hexenoic acid and the isopropanol was replaced by 0.48 g methanol. The reaction was conducted at a temperature of 170° and a pressure of 27.2 atm. After three hours the reaction product was cooled and recovered.

Analysis indicated 42.9% pimelic acid and 15.3% α-methyladipic acid based on the hexenoic acid charged. The linearity was 73.7%.

EXAMPLE 31

Example 1 was repeated, except that the 3-pentenoic acid was replaced by 27.64 g undecylenic acid and the isopropanol was replaced by 0.96 g methanol. The reaction was conducted at a temperature of 170° and a pressure of 27.2 atm. After about 3.5 hours the contents of the reactor were recovered as in Example 1.

Analysis indicated 41.9% conversion to dodecanedioic acid and 12.2% conversion to 2-methylundecanoic acid. The linearity was 77.4%.

EXAMPLE 32

Example 1 was repeated, except that the 3-pentenoic acid was replaced by 10.95 g acrylic acid and the isopropanol was replaced by 0.96 g methanol. The reaction was conducted at a temperature of 170° and a pressure of 27.2 atm for five hours following which the contents of the reactor were cooled and recovered. Carbon monoxide was being consumed when the reaction was terminated.

Analysis indicated 39.5% succinic acid based on acrylic acid charged. Linearity was 100% (no detectable methylmalonic acid).

EXAMPLE 33

Example 2 was modified as follows. The shaker tube was charged with a mixture of 4.25 g methyl iodide, 7.4 g 2-pentenoic acid, 2.7 g water, 0.19 g rhodium trichloride and 75 ml methylene chloride solvent. The tube was pressurized with 34 atm of carbon monoxide, heated to 220° over four hours then maintained at autogeneous pressure for an additional two hours.

Analysis of the product showed 17.8% adipic acid and 16.4% branched diacids (linearity - 51.9%) based on the 2-pentenoic acid charged.

TABLE I

| Example No. | Temperature (°C.) | Pressure (atm) | Adipic Acid | Methyl Glutaric Acid | Ethyl Succinic Acid | Valeric Acid | 2-pentenoic Acid | Gamma Valero-lactone | Conversion[2] % | Linearity[3] % |
|---|---|---|---|---|---|---|---|---|---|---|
| | | | | | Yield[1] (%) | | | | | |
| 2 | 140 | 27.2 | 59.2 | 25.1 | 1.0 | 1.1 | 1.6 | 9.6 | 99 | 69.4 |
| 3 | 150 | 27.2 | 61.0 | 20.8 | 1.0 | 0.6 | 0.6 | 11.3 | 100 | 73.7 |
| 4 | 160 | 27.2 | 66.0 | 20.2 | 0.7 | 0.9 | 0.9 | 10.7 | 100 | 76.0 |
| 5 | 170 | 27.2 | 60.6 | 14.4 | 0.4 | 1.5 | 2.1 | 9.4 | 80 | 80.3 |
| 6 | 180 | 27.2 | 61.2 | 11.0 | 0.3 | 6.4 | 4.8 | 5.8 | 65 | 84.5 |
| 7 | 160 | 40.8 | 64.6 | 18.6 | 0.8 | 0.3 | 1.2 | 13.5 | 99 | 77.0 |
| 8 | 170 | 40.8 | 64.2 | 19.6 | 0.8 | 0.9 | 0.8 | 16.4 | 100 | 75.9 |
| 9 | 180 | 40.8 | 56.8 | 17.5 | 0.7 | 0.4 | 1.1 | 15.1 | 100 | 75.7 |
| 10 | 140 | 27.2 | 42.3 | 33.9 | 5.3 | 1.0 | 2.7 | 8.1 | 100 | 51.9 |
| 11 | 160 | 27.2 | 51.0 | 25.2 | 1.9 | 0.7 | 4.1 | 7.5 | 97 | 65.3 |
| 12 | 170 | 27.2 | 53.8 | 16.0 | 1.0 | 0.6 | 4.6 | 2.9 | 70 | 76.1 |
| 13 | 140 | 34 | 41.8 | 34.1 | 6.9 | 0.9 | 2.4 | 11.0 | 99 | 50.5 |
| 14 | 150 | 34 | 41.1 | 33.4 | 5.8 | 1.3 | 2.6 | 11.1 | 99 | 51.2 |
| 15 | 160 | 34 | 45.9 | 28.8 | 4.9 | 1.9 | 2.8 | 12.0 | 98 | 57.6 |
| 16 | 170 | 34 | 50.6 | 19.1 | 1.6 | 1.0 | 5.7 | 12.0 | 85 | 70.9 |
| 17 | 140 | 40.8 | 39.5 | 31.0 | 6.1 | 0.9 | 1.9 | 13.9 | 100 | 51.6 |
| 18 | 150 | 40.8 | 38.1 | 29.7 | 6.6 | 1.4 | 1.4 | 12.8 | 100 | 51.2 |
| 19 | 160 | 40.8 | 49.0 | 30.0 | 5.7 | 2.1 | 1.3 | 15.0 | 100 | 57.8 |
| 20 | 170 | 40.8 | 45.0 | 23.8 | 4.2 | 2.4 | 1.7 | 14.7 | 100 | 61.6 |

[1] Yield = $\frac{\text{moles of compound}}{\text{moles of starting material}} \times 100$

[2] Conversion = % of starting material reacted

[3] Linearity = $\frac{\text{moles of adipic acid}}{\text{moles (adipic + α-methylglutaric + ethylsuccinic) acids}} \times 100$

I claim:

1. A process for the preparation of linear saturated dicarboxylic acids which comprises contacting an unsaturated monocarboxylic acid having the formula

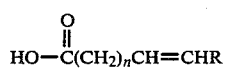

wherein R is selected from the class consisting of hydrogen, methyl and ethyl, n is 0–8 with carbon monoxide and water in the presence of a rhodium-containing catalyst, an iodide compound and a hydrolysis resistant saturated halocarbon solvent, except fluorocarbon, and mixtures thereof having 1-2 carbon atoms and when the solvent has two carbon atoms not more than two halogen atoms are attached to each carbon atom, at a temperature in the range of 100°-240° C. and a pressure in the range of 14-240 atmospheres while maintaining the concentration of water less than 4.3% by weight based upon the weight of the solvent.

2. The process of claim 1 wherein an alcohol having 1-6 carbon atoms is present in the reaction medium in the amount of 0.2-2.0 percent by weight based upon the halocarbon solvent.

3. The process of claim 1 wherein the solvent is methylene chloride.

4. The process of claim 2 wherein the solvent is methylene chloride.

5. The process of claim 1 wherein the unsaturated monocarboxylic acid is 3-pentenoic acid.

6. The process of claim 3 wherein the unsaturated monocarboxylic acid is 3-pentenoic acid.

7. The process of claim 1 wherein n=0-2.

8. The process of claim 3 wherein n=0-2.

* * * * *